(12) United States Patent
Dubey et al.

(10) Patent No.: US 8,609,163 B2
(45) Date of Patent: Dec. 17, 2013

(54) HERBAL FORMULATION ADVOCATED FOR THE PREVENTION AND MANAGEMENT OF CORONARY HEART DISEASE

(75) Inventors: Govind Prasad Dubey, Varanasi (IN);
Aruna Agarawal, Varanasi (IN);
Nirupama Dubey, Kattankulathur (IN);
Shipra Dubey, Kattankulathur (IN);
Rajesh Dubey, Kattankulathur (IN);
Samathanam Mercy Deborah, Varanasi (IN)

(73) Assignee: SRM University, Kattankulathur (IN)

( * ) Notice: Subject to any disclaimer, the term of this patent is extended or adjusted under 35 U.S.C. 154(b) by 0 days.

(21) Appl. No.: 13/206,306

(22) Filed: Aug. 9, 2011

(65) Prior Publication Data
US 2012/0034326 A1 Feb. 9, 2012

(30) Foreign Application Priority Data
Aug. 9, 2010 (IN) ............................ 2270/CHE/2010

(51) Int. Cl.
*A61K 36/00* (2006.01)
(52) U.S. Cl.
USPC ............ 424/773; 424/725; 424/775; 424/777
(58) Field of Classification Search
None
See application file for complete search history.

(56) References Cited

U.S. PATENT DOCUMENTS 6,153,198 A * 11/2000 Ghosal .......................... 424/773
2005/0266100 A1 * 12/2005 Sangwan et al. ............... 424/725

FOREIGN PATENT DOCUMENTS

| IN | 2610/MUM/2007 | | 1/2008 |
| IN | 226242 | | 1/2009 |
| WO | WO2010013254 | * | 2/2010 |
| WO | WO 2012/020422 | | 2/2012 |

OTHER PUBLICATIONS

Bavarva et al. (2008) Phytotherapy Res. 22, 620-626.*
Gao et al. (2000) J. Agric. Food Chem. 48, 1485-1490.*
Mohanty et al. (2008) Clinical Nutrition 27, 635-642.*
Suleyman et al. (2002) Biol. Pharm. Bull. 25(9), 1133-1136.*
Sultana et al. (2009) Molecules, 14, 2167-2180.*
Vijayalakshmi et al. (2008) Fitoterpia 197-198.*
Bhattacharya, et al. (1973) Jous. Res. Ind. Med. 8: 1-19.*
Chaman et al. (2011) Pak. J. Pharm. Sci., vol. 24, No. 3, pp. 345-351.*
Davis et al. (2000) J. Ethnopharmacology 71, pp. 193-200.*
Guliyev et al. (2004) J. Chromatography B, 812, 291-307.*
Mishra et al. (2000) Altern. Med. Rev. 5(4): 334-346.*
Negi et al. (2005) Food Chemistry 92, 119-124.*
Parmar et al. (2006) Parmazie 61: 793-795.*
Rajesh et al. (2009) J. Natural Remedies. vol. 9/2 235-241.*
Scassellati-Sforzolini et al. (1999) J. Environmental Pathology, Toxicology, and Oncology 18(2): 119-125.*
Singh et al. (2002) J. Med. Food vol. 5, No. 4, pp. 211-220.*
Sultana et al. (2007) Food Chemistry 104: 1106-1114.*
International Search Report Dated Sep. 27, 2011.
Third Party Submission dated Mar. 16, 2012.
Kaiyadeva; Kaiyadevanighantau—(Pathyapathyavibodhakah) Edited and translated by P.V. Sharma and Guru Prasad Sharma, Chaukhambha Orientalia, Varanasi, Edn. 1st, 1979, p. 193.
Mohammad Najmul Ghani Khan; Khazaain-al-Advia, vol. I (20th century AD), Nadeem Yunus Printer / Sheikh Mohd Basheer & Sons, Lahore, 1911 p. 503.
Bhiirata Bhaisajya Ratnakara—Compiled by Naginadasa Chaganalala Saha ,Translated by Gopinath Gupta—vol. I: B. Jain Publishers, New Delhi, Edn. 2nd. Reprint, Aug. 1999. p. 210.
Abdulla Sahib; Anuboga Vaithiya Navaneetham,Pub:Palani Thandayuthapani Devasthanam publications , Directorate of Indian systems of Medicine, Chennai.(1975) pp. 100-101.
Mohammad Najmul Ghani Khan; Khazaain-al-Advia, vol. II (20th century AD), Nadeem Yunus Printer / Sheikh Mohd Basheer & Sons, Lahore, 1911 p. 105-106.
Mohimmad Najmul Ghani Khan; Qaraabaadeen Najm-al-Ghani (20th century AD), Munshi Nawal Kishore, Lucknow, (Second Edition) 1928 p. 215.
Vangasena; Vangasena—Commentator Shaligram Vaisya, Edited Shankar Ialji Jain; Khemraj Shrikrishna Das Prakashan, Bombay, Edn. 1996 p. 1059.
Therayar; Therayar Kudineer.Pub: CCRAS Publications, Chennai. (1979) pp. 40-41.
Kandasamy Mudaliar; Athmarakshaamirtham, Pub: Ilakkana Achagam, Chennai (1975), pp. 539-540.
Brhat Nighantu Ratnakara (Saligramanighantubhusanam)—Compiled by Gangavisnu Srikr.sna Dasa, Translated by Sri Dattarama Srikrsnalala Mathura; vol. 4 (Part VII), edn. 1997, Khemaraja Srikrsnadas Prakasana, Mumbai-4, p. 186.
Dwivedi S et al: "Beneficial effects of *Terminalia arjuna* in coronary artery disease", Indian Heart Journal, Cardiological Society of India, Calcutta, IN, vol. 49, No. 5, Sep. 1, 1997, pp. 507-510.
Sandhu, et al."Effects of *Withania somnifera* (Ashwagandha) and *Terminalia arjuna* (Arjuna) on physical performance and cardiorespiratory endurance in healthy young adults", International Journal of Ayurveda Research, Bethesda MD : PUBMED, US, vol. 1, No. 3, Jul. 1, 2010, pp. 144-149.
Dwivedi Shridhar et al: "Modification of coronary risk factors by medicinal plants," Current Research on Medicinal and Aromatic Plants, Central Institute of Medicinal and Aromatic Plants, Lucknow, IN, vol. 22, No 1B, Mar. 1, 2000, pp. 616-620.
Basu et al: "Anti-atherogenic effects of seabuckthorn (Hippophaea rhamnoides) seed oil", Phytomedicine, Gustav Fischer Verlag, Stuttgart, DE, vol. 14, No. 11, Oct. 11, 2007, pp. 770-777.

* cited by examiner

*Primary Examiner* — Chris R Tate
*Assistant Examiner* — Russell Fiebig
(74) *Attorney, Agent, or Firm* — Venable LLP; Keith G. Haddaway

(57) ABSTRACT

According to this invention there a novel herbal formulation for the prevention and management of coronary heart disease and associated CHD risk factors, comprising, preparing a hydromethanolic extract of at least two plants selected from of *Withania somnifera, Costus speciosus, Hippophae rhamnoides* and *Terminalia arjuna* at 60-80° C., maintaining the pH of the solution between 7-10, separating the active compounds chromatographically, subjecting the active compounds to the step of molecular characterization.

12 Claims, 8 Drawing Sheets

HERBAL FORMULATION ADVOCATED FOR THE PREVENTION AND MANAGEMENT OF CORONARY HEART DISEASE

FIELD OF INVENTION

This invention relates to a novel herbal formulation advocated for the prevention and management of Coronary Heart Disease.

BACKGROUND OF INVENTION

In spite of tremendous advancement in the field of cardiovascular medicine and surgery the mobidity and mortality due to Coronary Heart Disease is still increasing in almost all the society. Worldwide attempt are being made to prevent coronary heart disease by modifying various risk factors. The alternate strategy that has gained wide spread application in the recent years is secondary prevention.

Coronary Heart Disease (CHD) is the leading cause of morbidity and mortality in many developed countries and will be an increasing problem for developing countries. Recognition of the alarming risk of CHD among South Asian Nations has led to take initiatives focusing on understanding of pathophysiological mechanisms and emphasis has been given on establishment of new remedial measures for cardio protection. Several but not all, of the known risk factors for CHD have been associated with a level of oxidative stress including use of tobacco, hypertension, dyslipidemia, obesity and diabetes. A production of oxidative stress, LDL-oxidation has been hypothesized as primary underlying mechanism for the development of atherosclerosis and CHD.

Abnormal blood lipid is the most important causative factor of Coronary Heart Disease. The association between serum cholesterol level and coronary heart disease is widely studied by several workers. Elevated serum Triglycerides and low HDL-c level is an independent risk factor of CHD.

Various epidemiological studies have shown that increased levels of serum lipoprotein (a), homocysteine, fibrinogen, insulin resistance and thrombogenic factors are strongly associated with the increased CHD risk. These fast emerging risk factors have strong genetic predisposition and have their beginning in early childhood. It showed presence of elevated markers like CRP and Homocysteine in school going children.

The level of homocysteine, a sulfydryl-containing amino acid and C-reactive protein (CRP), a protein found in the blood circulation, has shown to be predictive of future Coronary Heart Disease (CHD). There is also evidence that the elevated range of homocysteine and CRP concentration has association with atherosclerosis and thrombosis observed in many cases.

The American Heart Association and the Centre for Disease Control and prevention, released a scientific statement regarding clinical assessment of inflammatory markers IL-$_6$, TNF-α including CRP as a predictor for risk for cardiac event.

It has been observed in several cases and also among the patient suffered from vascular disease that, genetic factor influence plasma homocysteine concentration. It is also reported that homocysteine rise with age in both men and women and its concentration are higher in men than women. This may be due to difference in muscle mass and renal function. Sex hormones may also influence homocysteine concentration in plasma.

As pointed out earlier that elevated plasma homocysteine is a known factor for atherosclerotic vascular disease, it further increases the risk, associated with smoking and hypertension. Dietary regulation like folate, cobalamin and pyridoxal phosphate, modulate homocysteine metabolism.

Homocysteine level rise with decreasing concentration of vitamin $B_6$, vitamin $B_{12}$ and folate, further it increases due to their impaired metabolism by the kidneys and liver which enhances the risk of myocardial infarction and stroke. Certain drugs like
combination of colestipol and niacin, methotrexate, phenytoin carbomazepine and nitrous oxide may increase homocysteine concentration in plasma. Further, it is pointed out that patients with inherited defects of methionine metabolism can develop severe hyperhomocysteinemia and can have premature atherothrombosis. Though a mild to moderate elevation of homocysteine are common in general population due to insufficient dietary intake of folic acid.

Level of CRP is an acute phase marker and a predictor of the risk of atherosclerotic complication. High level of CRP is a significant marker of inflammation and it consistently predicts new coronary events in patients with unstable angina and acute myocardial infarction. It is reported that individuals with high-CRP levels has relative risks of future vascular events, three or four times higher than individuals with lower levels. Higher CRP may cause heart attack and is associated with lower survival rate of people. The other risk factors of CHD include lipoprotein remnants, lipoprotein (a), small LDL particles, HDL subspecies and various apolipoproteins including coronary calcium. It is widely accepted that evaluating CRP as a risk factor for CHD is of clinical significance in the prevention and management of CHD. High Body Mass Index (BMI) and insulin resistance are also contributing factors for CHD.

Resistin has been considered as one of the most important inflammatory markers responsible for endothelial dysfunction, atherosclerosis and cardiovascular disorder. Plasma resistin level are highly correlated with level of diverse inflammatory markers, particularly circulating TNF-α, IL-6, hs-CRP and lipoproteins. The resistin is directly associated with the level of adiponectin which has shown association with diabetes and Metabolic syndrome. Recent studies have demonstrated the association of adiponectin with diabetes mellitus and its potential anti-diabetic, anti-atherogenic and anti-inflammatory activities.

Psychological stress also plays an important role in precipitation of arterial hypertension, angina and myocardial infarction. Therefore stress management also contributes in the prevention of CHD.

Keeping the above background in to consideration it was decided to propose a safer remedial measure for the improvement in atherosclerotic process, reduction in high level of homocysteine and the inflammatory marker C-reactive protein, IL-6, resistin and abnormal lipids responsible for an adverse cardiac event.

Scientific evaluation of some of the Ayurvedic drugs have shown better efficacy over standard pharmacologic therapy as well as reduced side effects. The successful management of CHD is seldom possible with one drug alone. Generally it is observed that due to inadequate response of the drugs and troublesome side-effects the currently available drugs are not able to reduce the mortality and morbidity rate from CHD. It has long been recognized that the desirable action of the drugs conventionally used in CHD cases could be augmented and undesirable actions may be minimized by the use of two or more drugs in appropriate combination. In classical texts of Ayurveda many plant based drugs have been advocated for the prevention and management of cardiovascular disorders, without any adverse reaction. Ayurveda has given a comprehensive description about etiopathogenesis and management of coronary heart disease. Several single and combined formulations have been described in Ayurveda for the management of heart diseases. It includes all risk factors and their management. Taking the lead from ancient Indian literature it was thought to propose an Ayurveda formulation having multi-targeted action in CHD cases as well as CHD risk factors with the object to prevent the morbidity and mortality from CHD.

OBJECT OF INVENTION

The major object of present invention is to propose an Ayurveda plant based formulation beneficial in the prevention and management of risk factors causing Coronary Heart Disease in CHD cases as well as individuals at risk of development of CHD due to presence of CHD risk factors.

Another object of present invention is to propose a plant based Ayurveda formulation effective in the prevention and management of dyslipidemia by modifying abnormal lipids among cases at risk of CHD as well as established cases of CHD.

Another object of present invention is to propose a plant based formulation having triglyceride lowering property among CHD cases showing hypertriglyceridemia and also those individuals at risk of development of CHD due to elevated triglycerides.

Further, object is to propose a plant based formulation having potentiality in the regulation of blood pressure among CHD cases as well as cases of essential hypertension as hypertension is one of the major risk factors of CHD.

Still object is to propose a plant based Ayurveda formulation effective in the prevention and management of endothelial dysfunction by reducing atherosclerotic process among CHD cases as well as individuals at risk of development of CHD.

Still, another object of present invention is to propose a novel plant based Ayurveda formulation effective in reducing vascular inflammation by reducing pro-inflammatory cytokines TNF-α, IL-6, and also hs CRP and resistin among cases at risk of CHD and also diagnosed CHD cases.

Yet another object of present invention is to propose a plant based Ayurveda formulation having adiponectin enhancing and leptin lowering property.

Further, object of present invention is to propose a plant based Ayurveda formulation beneficial in reducing elevated homocysteine level, among cases at risk of CHD and also cases suffering from CHD.

Still, object is to propose a plant based Ayurveda formulation having anti-anxiety and anti-stress potential as anxiety and stress is one of the leading causes of CHD manifestation as well as precipitation of the disease condition.

STATEMENT OF INVENTION

According to this invention there is provided a novel plant based Ayurveda formulation beneficial in the prevention and management of coronary heart disease caused due to various CHD risk factors like atherosclerosis (dyslipidemia), obesity, impaired glucose tolerance (diabetes), Hyper-homocysteinemia, elevated inflammatory markers including resistin etc.

Further, according to this invention there is provided a process for the preparation of novel plant based Ayurveda formulation as claimed in Claim-I comprising of preparing hydro-methanolic extract of *Withania somnifera* (Ashwagandha—root), *Costus speciosus* (Kebuk—rhizome), *Terminalia arjuna* (Arjuna—bark) and *Hippophae rhamnoides* (Amlavetas—fruits) by using water (aqueous) and methanol (30:70) at 60-80° C. and maintaining pH of solution between 7-10, separating chromatographically the active compound present in each plant candidate by using TLC, HPLC and HPTLC supporting the molecular characterization of plant extract by using IR and NMR.

DETAILED DESCRIPTION OF THE INVENTION

Figure 1:
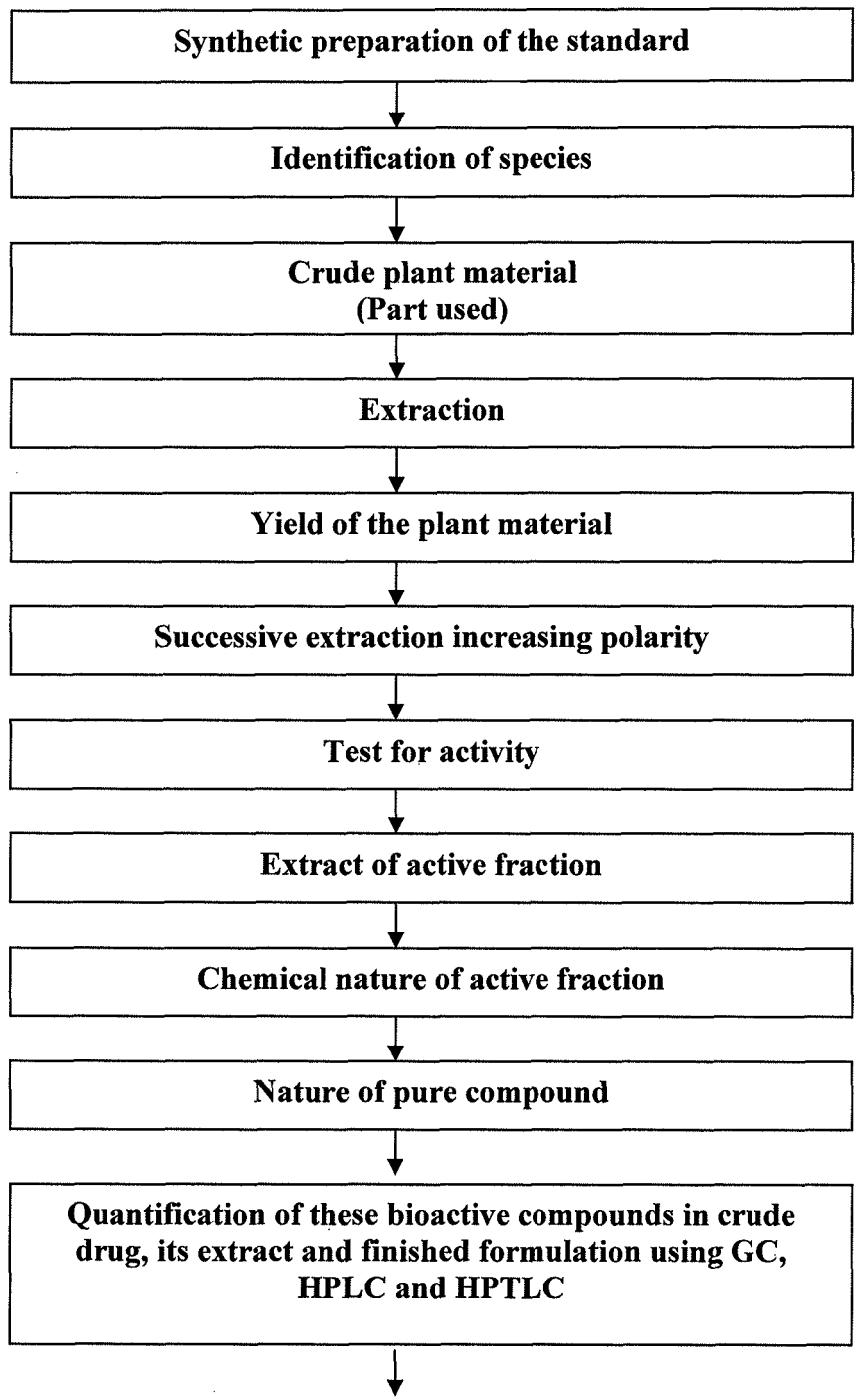
FIG. 1 is a flow diagram of the process.
Figure 1:
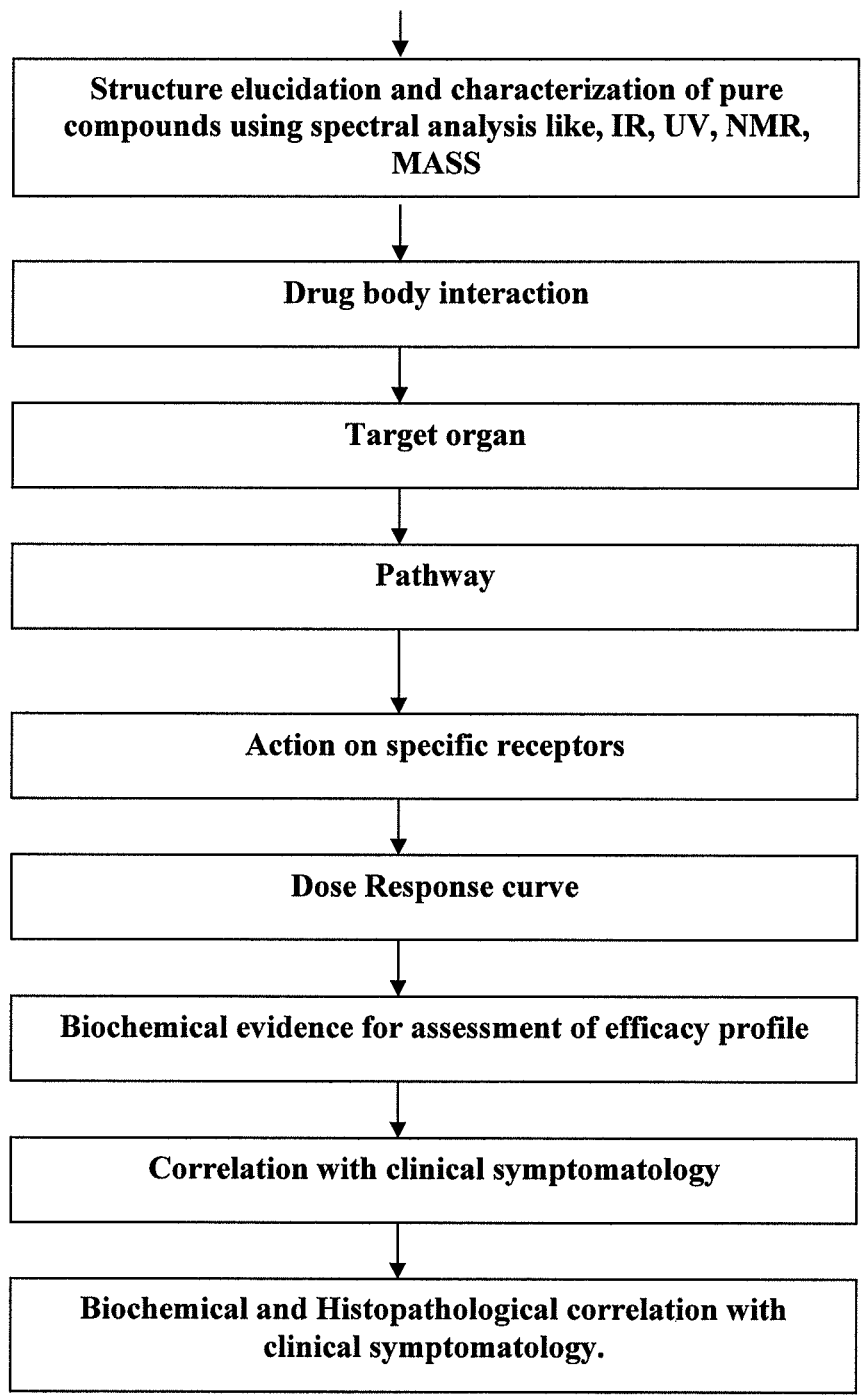

The present invention relates to a novel plant based Ayurveda formulation and the process thereof for the prevention and management of Coronary Heart Disease (CHD) particularly atherosclerosis. The preparation of present invention may be advantageous if used for the prevention and management of CHD risk factors like dyslipidemia, hypertension (atherosclerosis), obesity, hyper-homocysteinemia, diabetes mellitus etc. among the adult people. The beneficial effect of test formulation in diagnosed cases of CHD can be assessed on different fractions of lipids particularly oxidized LDL-c, HDL-c including triglycerides, inflammatory markers IL-6, TNF-α, resistin and CRP, adipokine, leptin and adiponectin, elevated homocysteine and also on some of the electrophysiological and psychological assessments.

The hydro-methanolic extract of four Ayurveda plants i.e. *Withania somnifera*, *Costus speciosus*, *Terminalia arjuna* and *Hippophae rhamnoides* by using 30:70 ratio of water and methanol respectively is utilized for the development of present novel formulation by conducting various experimental and clinical studies. The water utilized for extraction was decontaminated for any type of bacterial or abnormal growth by using reverse osmosis plant. After extraction the presence of active molecules in various plant extracts were identified by HPLC, HPTLC and NMR procedures.

The biological activity was studied on the basis of mode of action of single plant selected for preparation of combined formulation as well as combined formulation by assessing their role on various targets involved with CHD risk factors as well as already manifested CHD. The bio-molecular reaction following the interaction between the chemical and biological markers like abnormal lipids i.e. LDL-c, HDL-c, lipoprotein(a) and apolipo (B), Triglycerides, Homocysteine, Adiponectin, Leptin, inflammatory cytokines including resistin and also the neuropsychological assessments were evaluated.

The pre-clinical toxicological studies of single as well as combined formulation were carried out to determine safety profile of present novel test formulation. The efficacy profile of test formulation were done in pre-clinical animal model of high cholesterol diet induced dyslipidemia, cafeteria diet induced obesity, altered inflammatory markers particularly CRP and resistin etc. The mode of action of single plant candidate and combined formulation was determined in animal studies.

The beneficial role of present test formulation on abnormal lipids including lipoprotein (a) and apolipo (B), inflammatory biomarkers, adipocytes and plasma homocysteine concentrations were determined in various animal models before utilizing the drug for human use.

Extraction Procedure:

The dried root of *Withania somnifera*, rhizome of *Costus speciosus*, bark of *Terminalia arjuna* and fruits of *Hippophae rhamnoides*, were utilized for extraction. The hydro-methanolic extract of the plants were utilized for the identification of active compound present in the plants. After extraction, the extracted parts were taken for chromatographic HPLC, and HPTLC. After identification and separation of active compound, the molecular separation by using TLC, characterization was carried out by using IR and NMR.

The extraction was done at the temperature of 60-80° C. The pH of the solution was maintained between 7-10. The steps carried out to isolate the active compound to assess the activity of test formulation are shown in FIG. 1.

According to this invention, there is provided an Ayurveda formulation for the prevention and management of Coronary Heart Disease by modifying the CHD risk factors. The present test formulation comprising of the following ingredients:

| Name of the Plants | Parts used |
| --- | --- |
| 1. *Withania somnifera* (Ashwagandha) | root |
| 2. *Costus speciosus* (Kebuk) | rhizome |
| 3. *Terminalia arjuna* (Arjuna) | bark |
| 4. *Hippophae rhamnoides* (amlavetas) | fruits |

Preferably, the aforesaid plants are present in the formulation in the following doses—

| Name of the Plants | Dose range |
| --- | --- |
| 1. *Withania somnifera* | 200-425 mg/day |
| 2. *Costus speciosus* | 150-350 mg/day |
| 3. *Terminalia arjuna* | 225-450 mg/day |
| 4. *Hippophae rhamnoides* | 200-325 mg/day |

The formulation also comprise known additive such as minerals, vitamins, salts filler (for capsulation or to prepare syrup) and binders, if required to present in trace amount.

Thus any known additive or supplement is added to prepare the final formulation as required and present in trace amount. Reference is made here in capsule form (500 mg each). However, it would be apparent that the preparation may also be prepared in the form of syrup/tablet. Preferably but without implying any limitation the preparation comprises—

| Name of the plant | Dose |
| --- | --- |
| 1. *Withania somnifera* | 250 mg/day |
| 2. *Costus speciosus* | 200 mg/day |
| 3. *Terminalia arjuna* | 275 mg/day |
| 4. *Hippophae rhamnoides* | 225 mg/day |

Hypothesis:

The present plant based Ayurveda formulation is prepared out of four plant extract namely *Withania somnifera, Costus speciosus, Terminalia arjuna* and *Hippophae rhamnoides*. This formulation has been proven for its hypo-lipidemia, anti-atherosclerotic, anti-inflammatory, adiponectin enhancing homocysteine reducing and anti-anxiety activity among patients of CHD as well as individuals with positive evidence of CHD risk factors responsible for future development of CHD. Since coronary heart disease has a multi-factorial etiology it requires various drugs to manage the complex nature of disease. Therefore it was thought to validate a poly herbal formulation containing active compounds that acted on multi-targets involved in CHD.

The association between cardiovascular disease, lipid metabolism, obesity and adipokine signaling is of complex nature. A number of reference are available showing role of adipose tissue of an endocrine organ and secretion of adipokines i.e. leptin, adiponectin, resistin, ghrelin, visfatin that act on non-adipose tissues such as heart, diverse cellular and whole body function. These effects are mediated an increase in adiponectin and reduction in resistin level as low adiponectin and high resistin is associated with an increase in the risk of mortality due to CHD, and increase in adiponectin has been suggested to produce its protective effect via activation of cyclo-oxygenase-2 (COX-2) in cardiac myocytes, as inhibition of these enzyme resulted in the cardioprotective effects. Adiponectin also exerts anti-ischemic effects by increasing endothelial nitric oxide. Further, reduction in leptin reduces blood pressure through interaction with nitric oxide pathway. It is hypothesized that present novel test formulation acts through stimulation of endothelial nitric oxide by AMP activated protein kinase (AMPK) dependent mechanism as these have a favourable impact on micro-vascular functions.

The therapeutic intervention targets steps of atherosclerotic inflammation. Therapies include cytokine inhibitors, blockade of platelet derived growth factor (PDGF), cholesterol acetyl-transferase inhibition, anti-oxidant, anti-inflammatory agents and lipid lowering drugs. Cytokine inhibitors are anti-TNF-α antibodies. Inhibition of cytokine-stimulated PDGF, prevents accumulation of smooth muscle cells in atherosclerotic lesions and protection from plaque growth.

The ingredients combined in the test formulation have shown great potential in inhibiting platelet aggregation. It is proposed on the basis of results that perhaps the test drug reduced the formation of thromboxane, inhibited the phospholipase activity and lipoxygenase products formed in platelet.

Elevated levels of endothelin (ET) have been detected in patients with myocardial infarction. The test drug has shown blood pressure lowering effects due to decrease in peripheral vascular resistance. Test formulation modulates the production and function of both endothelium derived relaxation and constricting factors which causes protection against vasoconstriction. Thus, the test drug has vasodilatory activity as it inhibited endothelin to a great extent.

Hypercholesterolemia promotes endothelial dysfunction in the absence of atherosclerotic lesions. Endothelial dysfunction results in a decrease in nitric oxide bioavailability. Endothelial dysfunction can also direct formation of atherosclerotic lesions. The effect of present test formulation has been attributed to its capacity to reduce lipid content in arterial wall. The possible mechanism of test drug is that it causes direct anti-atherogenic and anti-atherosclerotic effects at the level of arterial wall. It depressed the hepatic activity of lipogenic and cholestrogenic enzyme like malic enzyme, fatty acid synthase and 3-hydroxy-3 methyl-glutaryl-CoA reductase.

Keeping the above facts in view and beneficial role of plants included in the present test formulation that acted on multiple targets involved in coronary heart disease and various CHD risk factors, determined in various pre-clinical models, it was thought to propose a safer remedial measure for the prevention and management of coronary risk factors involved with the onset of CHD so that morbidity and mortality due to CHD can be prevented/minimized.

About the Plant:

*Withania somnifera*: The plant belongs to family solanaceae, and is one of the ingredients of present test formulation. It has shown anti-stress, adoptogenic and hypotensive properties and is beneficial in the regulation of altered neurotransmitters through its active compound with anoloids, somniferine and withanine. One of the recent studies has indicated that *Withania somnifera* reconstruct the neuritic damage and also improves synaptic plasticity in the brain.

*Costus speciosus*: It belongs to family costaceae (zingiberaceae). It is also known as Keu, kusth. It is a succulent perennial herb growing up to 2.7 m. high. It is found through out the county in moist tropical forest. The rhizome contains tigogenin and diosgenin (2.6% diosgenin), α-amyrin, stearate, β-amyrin and lupeol palmitates from leaves have been isolated. Diosgenin and the mixture of five saponins obtained from the rhizome showed estrogenic effects in rats. The saponin mixture showed anti-inflammatory and anti-arthritic effects. The mixture of four alkaloids isolated from rhizome exhibited cardiotonic, diuretic and CNS depresent activities. The *Costus speciosus* root extract possess anti-hyperlipidemic, anti-hyperglycemic and anti-oxidative effects.

*Terminalia arjuna*: It belongs to Combretaceae family & commonly known as Arjuna. It is a deciduous tree found through out India, growing to height of 60-90 feet. The active constituents of *Terminalia arjuna* include tannins, triterpenoid saponins: Arjunic acid, Arjunolic acid, oleanolic acid, Arjungenin, Arjunin, Flavonoids: Arjunolone, Arjunone, Leuteolin, Steroids: B-Sitosterol and inorganic compounds.

In Ayurveda *Terminalia arujna* has been prescribed as cardio protective drug indicating its anti-atherosclerotic property. Several experimental and clinical evidence have proven the anti-atherosclerotic property of *Terminalia arjuna*. It is beneficial in the treatment of coronary artery disease, hypercholesterolemia dyslipidaemia including hypertriglyceridemia and anti-coagulant activity.

*Hippophae rhamnoides*: This is high altitude plant belongs to family Elaeagnaceae. Fruits and leaves have shown medicinal property. *Hippophae rhamnoides* is a rich source of flavonoids, vitamins, proteins, amino acids, folic acid, phytosterol, alpha-tocopherol and phenolic compounds. It has shown anti-oxidant, immuno-modulatory, anti-inflammatory and homocysteine lowering effects and uplifts the mental function.

Example-I

In experimental animal studies when the hydro-methanolic extract of *Terminalia arjuna* in the dose of 100 mg/kg/day and *Costus speciosus* in the dose of 75 mg/kg/day was administered to high cholesterol diet induced hypercholesterolemic rats for one month a significant reduction in total cholesterol, LDL-c with a moderate increase in HDL-c level was noticed which indicates anti-atherosclerotic and hypolipidemic potential of test drug. A decrease in TNF-α, IL-6 and CRP indicated the anti-inflammatory activity of the drug.

Example-II

When the hydro-methanolic extract of *Withania somnifera* in the dose of 80 mg/kg/day and *Hippophae rhamnoides* in the dose of 75 mg/kg/day and *Terminalia arjuna* in the dose of 75 mg/kg/day was mixed and given to obese rats a significant decrease in blood glucose level and triglycerides were measured following 30 days treatment.

Example-III

In clinical studies when the hydro-methanolic extract of *Terminalia arjuna* in the dose of 350 mg/day and *Costus speciosus* in the dose of 250 mg/day given to human subjects showing evidence of dyslipidemia, a decrease in total cholesterol, LDL-c and triglycerides were noticed. HDL-c level increased moderately in those cases indicating the hypo-lipidemic and cardio-protective activity of test drug.

Example-IV

When the hydro-methanolic extract of *Costus speciosus* in the dose of 275 mg/day and *Terminalia arjuna* in the dose of 350 mg/day was orally given to cases showing triglycerides 200 mg/dl and above, a marked decrease in the level was noticed, hs CRP level also decreased to a significant level in this group of study.

Example-V

When the hydro-methanolic extract of *Withania somnifera* in the dose of 325 mg/day, *Hippophae rhamnoides* in the dose of 300 mg/day and *Costus speciosus* in the dose of 250 mg/day mixed and given to cases showing high blood pressure a decreased in both systolic and diastolic blood pressure indicated the anti-hypertensive and anti-atherogenic effects of the drug. Further, the leptin level also decreased following treatment, which also supported the regulation of blood pressure.

Example-VI

When the hydro-methanolic extract of *Hippophae rhamnoides* in the dose of 250 mg/day, *Costus speciosus* in the dose of 325 mg/day and *Terminalia arjuna* in the dose of 225 mg/day mixed and given to CHD cases showing high level of inflammatory cytokines IL-6 and TNF-α a decrease in the level suggested the anti-inflammatory activity of the drug. Further, retard in hs CRP and resistin also confirmed the improved endothelial inflammation in those subjects.

Example-VII

When the hydro-methanolic extract of *Costus speciosus* in the dose of 325 mg/day and *Withania somnifera* in the dose of 350 mg/day mixed and given to CHD cases showing, low adiponectin and high leptin an increase in adiponectin and decrease in leptin level indicated the anti-atherogenic activity of test formulation. Body mass index also reduced following treatment with test formulation.

Example-VIII

When the hydro-methanolic extract of *Hippophae rhamnoides* in the dose of 325 mg/day and *Withania somnifera* in the dose of 325 mg/day was mixed and orally administered to cases suffering from CHD and showing elevated level of homocysteine, decrease in the homocysteine level indicated the anti-atherosclerotic effects resulting in reduced risk of onset of CHD as well as precipitation of CHD complications.

Example-IX

When the hydro-methanolic extract of *Withania somnifera* in the dose of 375 mg/day and *Hippophae rhamnoides* in the dose of 275 mg/day mixed and given to cases suffering from CHD and showing high anxiety level with high muscle action potential, the test drug exerted significant reduction in anxiety and stress with improvement in sleep pattern in those patients.

Example-X

A better and promising results were obtained when the hydro-methanolic extract of *Withania somnifera* in the dose of 250 mg/day, *Costus speciosus* in the dose of 200 mg/day, *Terminalia arjuna* in the dose of 275 mg/day and *Hippophae rhamnoides* in the dose of 225 mg/day mixed and given to diagnosed CHD patients or subjects showing presence of CHD risk factors, modification in abnormal lipids including Lipoprotein(a) and Apolipo (B), reduction in triglycerides, reduction in inflammatory cytokines and adipokines and reduced homocysteine with improvement in endothelial dysfunction were noticed. As synergistic effects this combination exerted anti-stress, anti-anxiety and anti-oxidant activity. A general feeling of well being was reported by most of the cases.

The non-clinical and clinical safety profile assessment indicated that the drug is safe and can be given for longer time without any adverse reaction.

Experimental Evidence

Anti-Obesity Role of Test Formulation
Animal—female Wistar rats—6 in each group
Weight—95-125 gm.
Group-I: Normal control
Group-II: Treated with Cafeteria diet
Group-III: Treated with cafeteria diet+test formulation
Cafeteria Diet:
  1st day—condensed milk 40 gm.+bread 40 gm.
  2nd Day—Chocolate 15 gm+biscuits 30 gm+dried coconut 30 gm.
  3rd day—Cheese 40 gm+boiled potato 50 gm (Repeated successively up to 30 days and given to 6 rats of Group-II & III)
Parameters:
Body wt., blood glucose, TC & TG, Adiponectin.
Test formulation was suspended in distilled water and administered orally in a dose of 300 mg./kg P.O. twice in a day at a constant volume of 0.5 ml/100 gm. wt. for 30 days

TABLE 1

Effect of test formulation on body wt. following cafeteria diet in experimental rats

| Groups | Body weight (gm) | | | Comp. Initial vs after 30 days |
|---|---|---|---|---|
| | Initial | After 15 days | After 30 days | |
| Normal control (N = 6) | 104.93 ± 3.88 | 110.82 ± 6.03 | 117.36 ± 4.91 | $P < 0.001$ |
| Cafeteria diet only (N = 6) | 99.22 ± 4.37 | 128.92 ± 6.11 | 158.90 ± 12.13 | $P < 0.001$ |
| Cafeteria diet + test formulation (N = 6) | 112.38 ± 10.45 | 126.74 ± 7.90 | 137.08 ± 9.31 | $P < 0.001$ |

TABLE 2

Effect of test formulation on total cholesterol and triglycerides following cafeteria diet in experimental animals

| Groups | TC (mg/dl) | | Comp. inital vs after 30 days | Triglyceride (mg/dl) | | Comp. initial vs after 30 days |
|---|---|---|---|---|---|---|
| | Initial | After 30 days | | Initial | After 30 days | |
| Normal Control (N = 6) | 84.78 ± 4.69 | 88.36 ± 5.11 | $P > 0.05$ | 81.89 ± 8.63 | 83.01 ± 9.34 | $P > 0.05$ |
| Cafeteria diet only (N = 6) | 87.11 ± 6.94 | 91.35 ± 9.12 | $P < 0.05$ | 79.74 ± 5.80 | 98.34 ± 4.93 | $P < 0.05$ |
| Cafeteria diet + test formulation (N = 6) | 83.98 ± 7.13 | 79.45 ± 5.90 | $P < 0.05$ | 81.04 ± 5.82 | 77.83 ± 6.71 | $P < 0.05$ |

TABLE 3

Effect of test formulation on blood glucose level and adiponectin following cafeteria diet in experimental animals

| Groups | Blood glucose level (mg/dl) Initial | After 30 days | Comp. initial vs after 30 days | Adiponectin (μg/ml) Initial | After 30 days | Comp. initial vs After 30 days |
|---|---|---|---|---|---|---|
| Normal control (N = 6) | 58.90 ± 7.02 | 55.70 ± 6.88 | P > 0.05 | 12.87 ± 1.91 | 13.16 ± 2.08 | P > 0.05 |
| Cafeteria diet only (N = 6) | 54.93 ± 6.12 | 71.11 ± 5.90 | P < 0.001 | — | 7.82 ± 1.03 | P < 0.001 |
| Cafeteria diet + test formulation (N = 6) | 57.91 ± 5.16 | 63.90 ± 4.23 | P < 0.01 | — | 9.37 ± 1.52 | P < 0.01 |

Anti-Atherogenic Effect of Test Formulation

Role of Test formulation on TC among high cholesterol diet treated rats

| Groups | Total cholesterol level (mg/dl) Initial | after 15 day | after 1 month |
|---|---|---|---|
| Normal control (N = 10)* | 64.32 ± 7.89 | 63.80 ± 6.52 | 64.70 ± 8.42 |
| High cholesterol diet (N = 10)** | — | 895.42 ± 49.75 | 480.82 ± 40.72 |
| High cholesterol diet + Test formulation (N = 10)*** | — | 738.44 ± 90.85 | 378.50 ± 38.20 |
| High cholesterol diet + statin (2.5 mg/kg/day) (N = 10)**** | — | 691.52 ± 78.85 | 280.50 ± 16.80 |
| Comparison | | | |
| * vs** | P > 0.05 | P < 0.001 | P < 0.001 |
| ** vs*** | | P < 0.001 | P < 0.001 |
| *** vs **** | | P < 0.001 | P < 0.001 |

Effect of Test formulation on LDL-c level among high cholesterol diet treated rats

| Groups | LDL-c level (mg/dl) Initial | after 15 day | after 1 month |
|---|---|---|---|
| Normal control (N = 10)* | 23.85 ± 4.78 | 22.75 ± 5.72 | 24.22 ± 6.85 |
| High cholesterol diet (N = 10)** | — | 341.50 ± 62.32 | 314.40 ± 48.34 |
| High cholesterol diet + Test formulation (N = 10)*** | — | 274.50 ± 41.93 | 142.55 ± 32.08 |
| High cholesterol diet + Statin (2.5 mg/kg/day) (N = 10)**** | — | 255.80 ± 37.38 | 108.85 ± 16.85 |
| Comparison | | | |
| * vs** | P > 0.05 | P < 0.001 | P < 0.001 |
| ** vs*** | | P < 0.05 | P < 0.001 |
| *** vs **** | | P > 0.05 | P < 0.05 |

Effect of Test formulation on HDL-c level among high cholesterol diet treated rats

| Groups | HDL-c level (mg/dl) Initial | after 15 day | after 1 month |
|---|---|---|---|
| Normal control (N = 10)* | 22.50 ± 4.33 | 23.32 ± 2.85 | 22.37 ± 3.85 |
| High cholesterol diet (N = 10)** | — | 17.82 ± 5.32 | 13.85 ± 1.85 |
| High cholesterol diet + Test formulation (N = 10)*** | — | 19.60 ± 3.85 | 21.20 ± 3.85 |
| High cholesterol diet + Statin (2.5 mg/kg/day) (N = 10)**** | — | 20.32 ± 4.85 | 21.85 ± 3.85 |
| Comparison | | | |
| * vs** | P > 0.05 | P < 0.05 | P < 0.001 |
| ** vs*** | | P > 0.05 | P < 0.001 |
| *** vs **** | | P > 0.05 | P < 0.05 |

Effect of Test formulation on Triglycerides level among high cholesterol diet treated rats

| Groups | Triglycerides level (mg/dl) Initial | after 15 day | after 1 month |
|---|---|---|---|
| Normal control (N = 10)* | 26.85 ± 8.70 | 30.32 ± 7.85 | 28.40 ± 5.52 |
| High cholesterol diet (N = 10)** | — | 340.70 ± 64.80 | 298.50 ± 39.32 |
| High cholesterol diet + Test formulation (N = 10)*** | — | 260.55 ± 69.85 | 174.93 ± 21.78 |
| High cholesterol diet + Statin (2.5 mg/kg/day) (N = 10)**** | — | 228.50 ± 31.80 | 112.85 ± 19.30 |
| Comparison | | | |
| * vs** | P > 0.05 | P < 0.001 | P < 0.001 |
| ** vs*** | | P < 0.05 | P < 0.01 |
| *** vs **** | | P > 0.05 | P < 0.05 |

Clinical Evidence

TABLE 1

Effect of test formulation on Total Cholesterol among CHD cases

| Treatment Groups | No. of Cases | Total cholesterol (mg/dL) | | | |
|---|---|---|---|---|---|
| | | Initial | After 3 Months therapy | After 6 Months therapy | Comp. Initial vs After 6 months therapy |
| Treated with Statin | 47 | 285.71 ± 53.80 | 200.90 ± 40.35 | 214.73 ± 39.65 | T = 7.28<br>$P < 0.001$ |
| Treated with Test Formulation | 52 | 296.93 ± 64.71 | 255.98 ± 51.69 | 231.82 ± 38.44 | T = 6.24<br>$P < 0.001$ |

Normal range: <200 mg/dl

Figure 2:
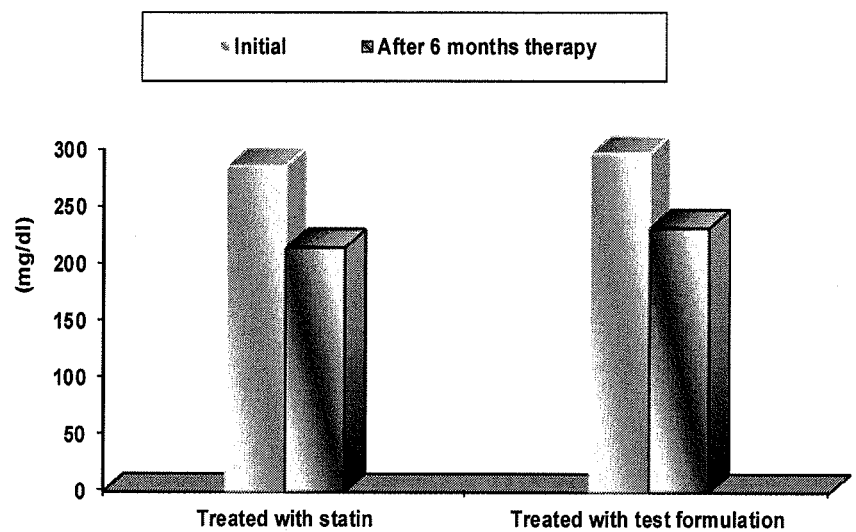
FIG. 2 is showing the effect of test formulation on Total Cholesterol among CHD cases.

Results of the effect of test formulation on Total Cholesterol among CHD cases are shown in FIG. 2.

TABLE 2

Effect of test formulation on LDL-c among CHD cases

| Treatment Groups | No. of Cases | LDL-c(mg/dL) | | | |
|---|---|---|---|---|---|
| | | Initial | After 3 Months therapy | After 6 Months therapy | Comp. Initial vs After 6 months therapy |
| Treated with Statin | 47 | 141.72 ± 11.30 | 128.76 ± 10.54 | 104.93 ± 9.45 | T = 17.19<br>$P < 0.001$ |
| Treated with Test Formulation | 52 | 146.94 ± 9.73 | 132.65 ± 8.88 | 123.88 ± 7.165 | T = 13.80<br>$P < 0.001$ |

Normal range: ≤100 mg/dl

Figure 3:
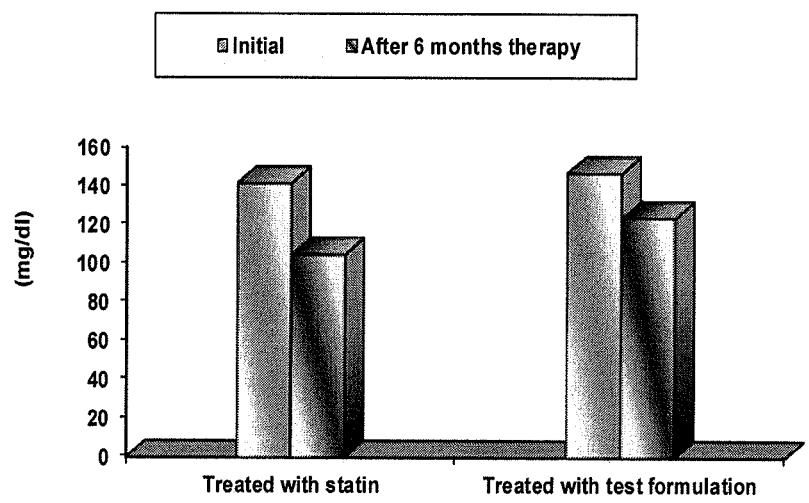
FIG. 3 is showing the effect of test formulation on LDL-c among CHD cases.

Results of the Effect of test formulation on LDL-c among CHD cases are shown in FIG. 3.

TABLE 3

Effect of test formulation on HDL-c content among CHD cases

| Treatment Groups | No. of Cases | HDL-c (mg/dl) | | | |
|---|---|---|---|---|---|
| | | Initial | After 3 Months therapy | After 6 Months therapy | Comp. Initial vs After 6 months therapy |
| Treated with Statin | 47 | 37.81 ± 3.19 | 40.34 ± 3.87 | 44.73 ± 2.84 | T = 11.34<br>$P < 0.001$ |
| Treated with Test Formulation | 52 | 36.14 ± 2.75 | 38.44 ± 3.01 | 40.98 ± 3.13 | T = 8.49<br>$P < 0.001$ |

Normal range: ≥45 mg/dl

Figure 4:
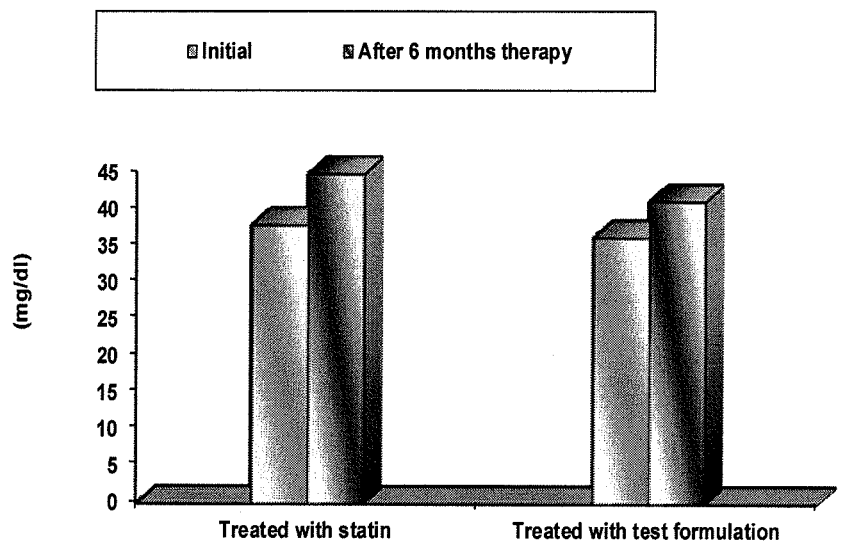
FIG. 4 is showing the effect of test formulation on HDL-c content among CHD cases.

Results of the effect of test formulation on HDL-c content among CHD cases are shown in FIG. 4.

TABLE 4

Effect of test formulation on Triglycerides content among CHD cases [7]

| Treatment Groups | No. of Cases | Triglycerides (mg/dl) | | | |
|---|---|---|---|---|---|
| | | Initial | After 3 Months therapy | After 6 Months therapy | Comp. Initial vs After 6 months therapy |
| Treated with Statin | 47 | 564.84 ± 88.64 | 435.65 ± 87.35 | 375.91 ± 93.75 | T = 10.04<br>$P < 0.001$ |

TABLE 4-continued

Effect of test formulation on Triglycerides content among CHD cases [7]

| Treatment Groups | No. of Cases | Triglycerides (mg/dl) | | | |
| --- | --- | --- | --- | --- | --- |
| | | Initial | After 3 Months therapy | After 6 Months therapy | Comp. Initial vs After 6 months therapy |
| Treated with Test Formulation | 52 | 498.73 ± 102.64 | 409.65 ± 99.65 | 361.82 ± 75.44 | T = 7.75 P < 0.001 |

Normal range: ≤150 mg/dl

Figure 5:
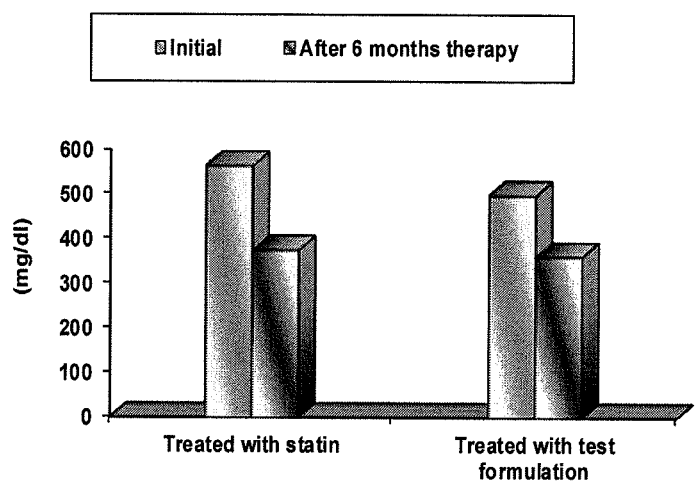
FIG. 5 is showing the effect of test formulation on Triglycerides content among CHD cases.

Results of the Effect of test formulation on Triglycerides content among CHD cases are shown in FIG. 5.

TABLE 5

Decrease in Apolipo (B) following Ayurveda test formulation in CHD cases

| Treatment Groups | No. of Cases | Apolipo (B) (mg/dl) | | | |
| --- | --- | --- | --- | --- | --- |
| | | Initial | After 3 Months therapy | After 6 Months therapy | Comp. Initial vs After 6 months therapy |
| Treated with Statin | 47 | 184.73 ± 42.33 | 162.98 ± 38.56 | 143.75 ± 35.28 | T = 5.10 P < 0.001 |
| Treated with Test Formulation | 52 | 198.75 ± 38.43 | 182.54 ± 34.36 | 158.85 ± 31.16 | T = 5.81 P < 0.001 |

Normal range: 55-159 mg/dl

Figure 6:
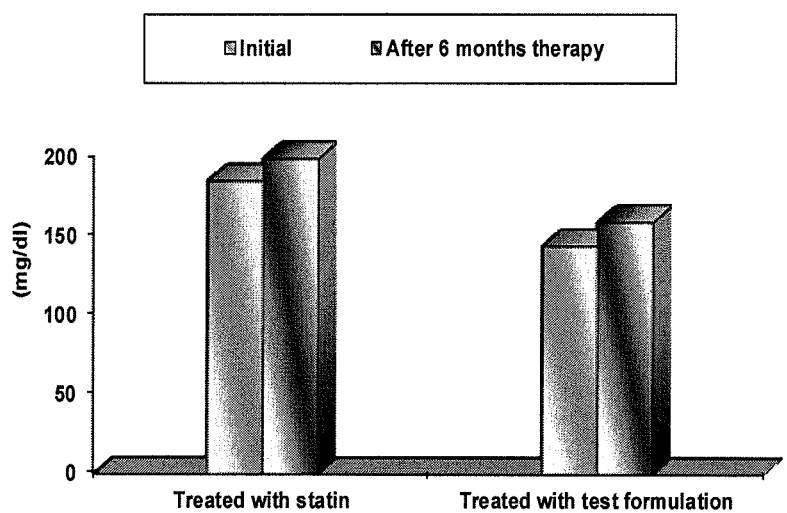
FIG. 6 is showing the effect of the decrease in Apolipo (B) following Ayurveda test formulation in CHD cases.

Results of the effect of Decrease in Apolipo (B) following Ayurveda test formulation in CHD cases are shown in FIG. 6.

TABLE 6

Decrease in Lipoprotein (a) following Ayurveda test formulation among CHD cases

| Treatment Groups | No. of Cases | Lipoprotein (a) (mg/dl) | | | |
| --- | --- | --- | --- | --- | --- |
| | | Initial | After 3 Months therapy | After 6 Months therapy | Comp. Initial vs After 6 months therapy |
| Treated with Statin | 47 | 22.87 ± 5.46 | 19.65 ± 4.63 | 17.35 ± 3.75 | T = 5.75 P < 0.001 |
| Treated with Test Formulation | 52 | 27.03 ± 6.91 | 25.32 ± 5.55 | 23.82 ± 4.13 | T = 2.89 P < 0.01 |

Normal range: 15-30 mg/dl

Figure 7:
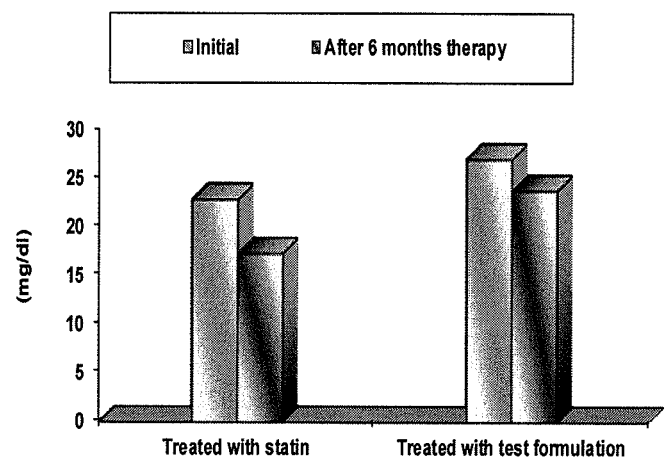
FIG. 7 is showing the effect of the decrease in Lipoprotein (a) following Ayurveda test formulation among CHD cases.

Results of the Decrease in Lipoprotein (a) following Ayurveda test formulation among CHD cases are shown in FIG. 7.

TABLE 7

Effect of test formulation on Endothelin among CHD cases

| Treatment Groups | No. of Cases | Endothelin (pg/ml) | | | |
| --- | --- | --- | --- | --- | --- |
| | | Initial | After 3 Months therapy | After 6 Months therapy | Comp. Initial vs After 6 months therapy |
| Treated with Statin | 47 | 1223.75 ± 209.00 | 1125.54 ± 176.27 | 1012.98 ± 163.84 | T = 5.44 P < 0.001 |

TABLE 7-continued

Effect of test formulation on Endothelin among CHD cases

| Treatment Groups | No. of Cases | Endothelin (pg/ml) | | | |
|---|---|---|---|---|---|
| | | Initial | After 3 Months therapy | After 6 Months therapy | Comp. Initial vs After 6 months therapy |
| Treated with Test Formulation | 52 | 1498.35 ± 196.285 | 1208.48 ± 201.22 | 1182.77 ± 158.87 | T = 9.01 P < 0.001 |

Normal range: 0.32-1000 pg/ml

Figure 8:
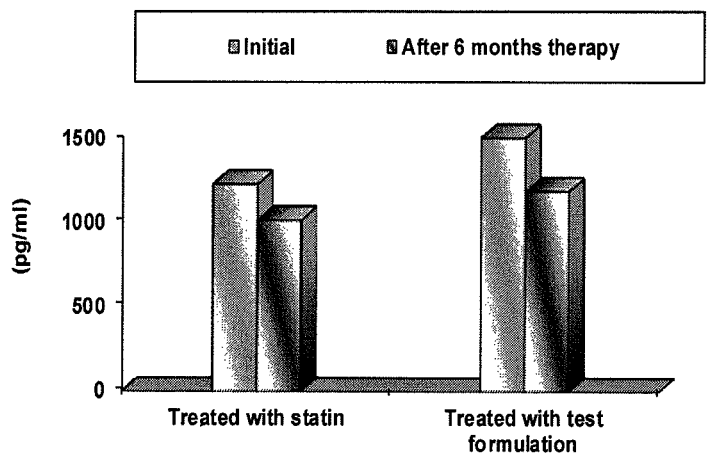
FIG. 8 is showing the effect of test formulation on Endothelin among CHD cases.

Results of the effect of test formulation on Endothelin among CHD cases are shown in FIG. 8.

TABLE 8

Decrease in Interleukin-6 inflammatory marker among CHD cases following test drug treatment.

| Treatment Groups | No. of Cases | Interleukin-6 (pg/ml) | | | |
|---|---|---|---|---|---|
| | | Initial | After 3 Months therapy | After 6 Months therapy | Comp. Initial vs After 6 months therapy |
| Treated with Statin | 47 | 2.32 ± 0.48 | 1.86 ± 0.62 | 1.09 ± 0.59 | T = 11.18 P < 0.001 |
| Treated with Test Formulation | 52 | 2.09 ± 0.51 | 1.82 ± 0.60 | 1.42 ± 0.48 | T = 7.44 P < 0.001 |

Normal range: <1 pg/ml

Figure 9:
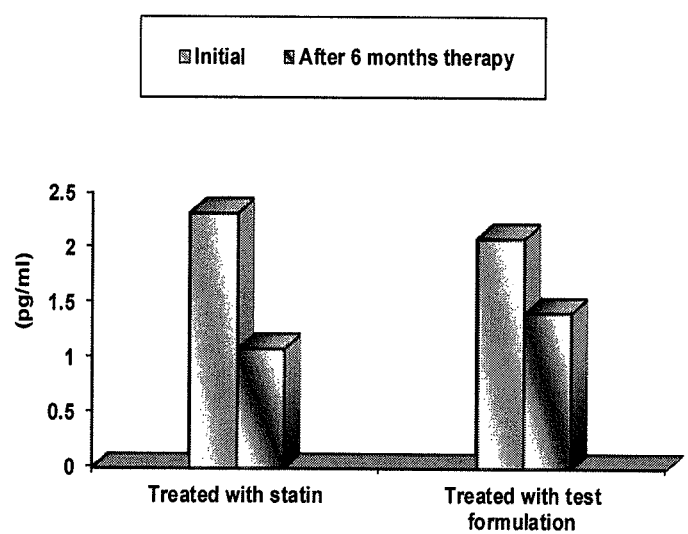
FIG. 9 is showing the effect of the decrease in Interleukin-6 inflammatory marker among CHD cases following test drug treatment.

Results of the Decrease in Interleukin-6 inflammatory marker among CHD cases following test drug treatment are shown in FIG. 9.

TABLE 9

Reduction in TNF-α inflammatory marker following test drug treatment among CHD cases

| Treatment Groups | No. of Cases | TNF-α (pg/ml) | | | |
|---|---|---|---|---|---|
| | | Initial | After 3 Months therapy | After 6 Months therapy | Comp. Initial vs After 6 months therapy |
| Treated with Statin | 47 | 632.11 ± 68.91 | 585.32 ± 80.32 | 439.78 ± 76.02 | T = 12.85 P < 0.001 |
| Treated with Test Formulation | 52 | 673.12 ± 78.61 | 634.35 ± 69.05 | 568.75 ± 51.02 | T = 8.03 P < 0.001 |

Normal range: 25-800 pg/ml

Figure 10:
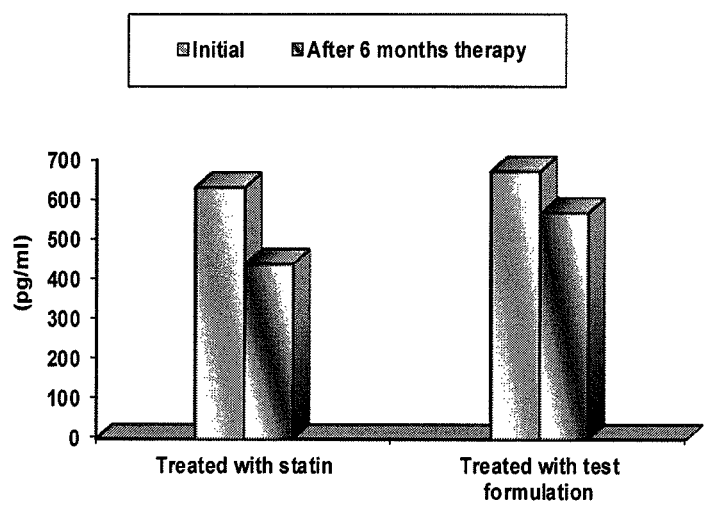
FIG. 10 is showing the effect of the reduction in TNF-α inflammatory marker following test drug treatment among CHD cases.

Results of the Reduction in TNF-α inflammatory marker following test drug treatment among CHD cases are shown in FIG. 10.

TABLE 10

Decrease in plasma resistin level following Ayurvedic test formulation among CHD cases.

| Treatment Groups | No. of Cases | Resistin (ng/ml) | | | |
|---|---|---|---|---|---|
| | | Initial | After 3 Months therapy | After 6 Months therapy | Comp. Initial vs After 6 months therapy |
| Treated with Statin | 33 | 12.98 ± 3.22 | 10.45 ± 2.73 | 10.01 ± 2.85 | T = 4.00 P < 0.001 |

TABLE 10-continued

Decrease in plasma resistin level following Ayurvedic test formulation among CHD cases.

| Treatment Groups | No. of Cases | Resistin (ng/ml) | | | |
|---|---|---|---|---|---|
| | | Initial | After 3 Months therapy | After 6 Months therapy | Comp. Initial vs After 6 months therapy |
| Treated with Test Formulation | 41 | 14.10 ± 4.21 | 11.62 ± 2.95 | 9.22 ± 3.59 | T = 5.65 P < 0.001 |

Normal range: 3-8 ng/ml

Figure 11:
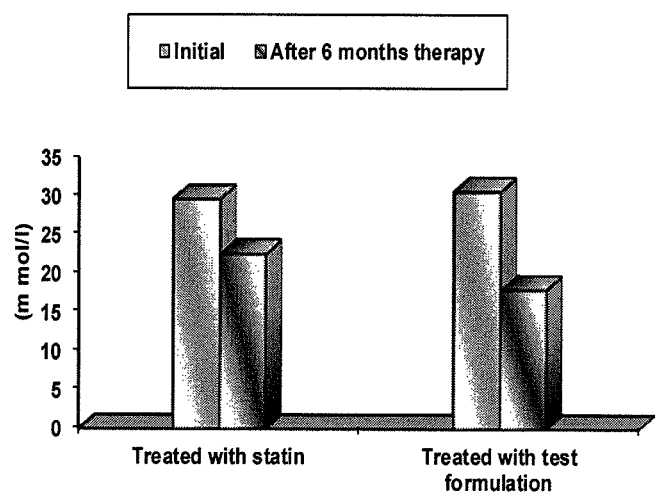
FIG. 11 is showing the effect of the decrease in plasma resistin level following Ayurvedic test formulation among CHD cases.

Results of the decrease in plasma resistin level following Ayurvedic test formulation among CHD cases are shown in FIG. 11.

TABLE 11

Decrease in plasma Homocysteine level following Ayurvedic test formulation among CHD cases.

| Treatment Groups | No. of Cases | Homocysteine (mmol/l) | | | |
|---|---|---|---|---|---|
| | | Initial | After 3 Months therapy | After 6 Months therapy | Comp. Initial vs After 6 months therapy |
| Treated with Statin | 47 | 29.72 ± 6.22 | 26.32 ± 5.10 | 22.62 ± 5.12 | T = 6.06 P < 0.001 |
| Treated with Test Formulation | 52 | 30.71 ± 7.91 | 26.62 ± 5.32 | 18.02 ± 6.92 | T = 8.75 P < 0.001 |

Normal range: 5-15 μmol/L

Figure 12:
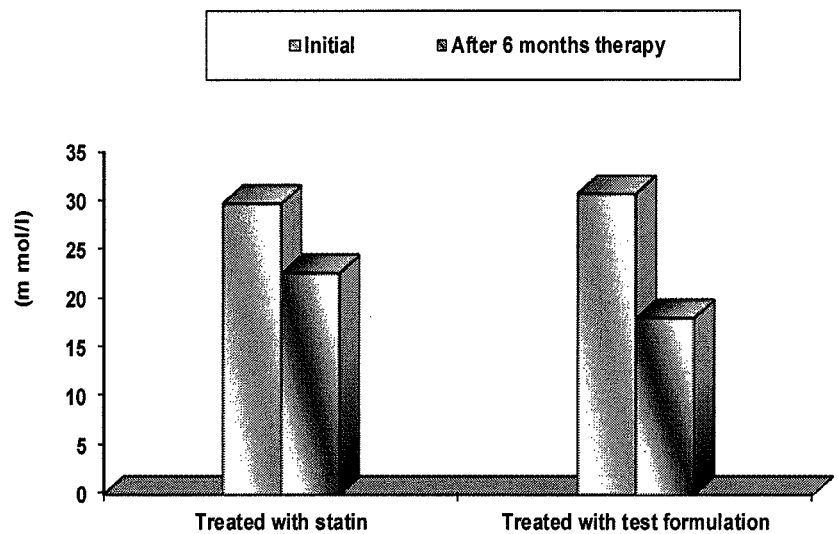
FIG. 12 is showing the effect of the decrease in plasma Homocysteine level following Ayurvedic test formulation among CHD cases.

Results of the Decrease in plasma Homocysteine level following Ayurvedic test formulation among CHD cases are shown in FIG. 12.

TABLE 12

Effect of test formulation on Brachial Artery thickening among CHD cases

| Treatment Groups | No. of Cases | Brachial artery thickening (mm) | | | |
|---|---|---|---|---|---|
| | | Initial | After 3 Months therapy | After 6 Months therapy | Comp. Initial vs After 6 months therapy |
| Treated with Statin | 47 | 3.42 ± 0.08 | 3.26 ± 0.09 | 3.12 ± 0.06 | T = 30.00 P < 0.001 |
| Treated with Test Formulation | 52 | 3.81 ± 0.10 | 3.68 ± 0.11 | 3.24 ± 0.11 | T = 28.50 P < 0.001 |

Figure 13:
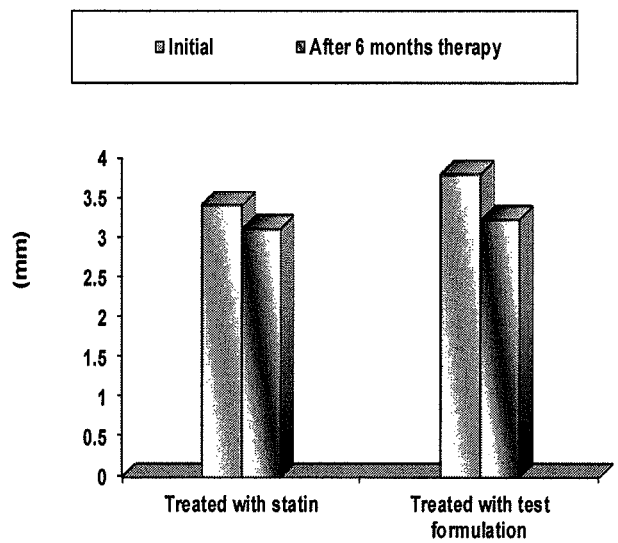
FIG. 13 is showing the effect of test formulation on Brachial Artery thickening among CHD cases.

Results of the effect of test formulation on Brachial Artery thickening among CHD cases are shown in FIG. 13.

We claim:

1. A dosage formulation for reducing coronary heart disease disease (CHD) and associated CHD risk factors in a patient having CHD or at risk for developing CHD, wherein the dosage formulation comprises effective amounts of *Withania somnifera, Costus speciosus, Hippophae rhamnoides* and *Terminalia arjuna* hydromethanolic extracts.

2. The dosage formulation of claim 1, wherein the extracts are from the plant parts:

| 1. | *Withania somnifera* (Ashwagandha) | root |
| 2. | *Costus speciosus* (Kebuk) | rhizome |
| 3. | *Terminalia arjuna* (Arjuna) | bark |
| 4. | *Hippophae rhamnoides* (Amlavetas) | fruits. |

3. The dosage formulation of claim 1, wherein the extracts are present in an amount to provide doses of:

| 1. | *Withania somnifera* (Ashwagandha) | 200-425 mg/day |
| 2. | *Costus speciosus* (Kebuk) | 150-350 mg/day |

-continued

| 3. | *Terminalia arjuna* (Arjuna) | 225-450 mg/day |
| 4. | *Hippophae rhamnoides* (Amlavetas) | 200-325 mg/day. |

4. The dosage formulation of claim 3 wherein the extracts are present in the amount to provide doses of:

| 1. | *Withania somnifera* (Ashwagandha) | 250 mg/day |
| 2. | *Costus speciosus* (Kebuk) | 200 mg/day |
| 3. | *Terminalia arjuna* (Arjuna) | 275 mg/day |
| 4. | *Hippophae rhamnoides* (Amlavetas) | 225 mg/day. |

5. The dosage formulation of claim 1, wherein the effective dose reduces one or more risk factors or markers of CHD selected from the groups consisting of hypolipidemic effect, anti-atherogenic effects, reduction of vascular inflammation, total cholesterol lowering, LDL-c lowering, cholesterol HDL-C increasing, and reducing hyper-triglyceridemia.

6. The dosage formulation of claim 1, wherein the effective dose reduces one or more risk factors or marker of coronary heart disease selected from the group consisting of homocysteine lowering property among the individuals showing hyper-Hcy level and anti-stress or anti-anxiety effects to improve sleep pattern.

7. The dosage formulation of claim 1, wherein the effective dose reduces one or more risk factors or markers of coronary heart disease selected from the group consisting of lowering blood glucose and reducing triglycerides.

8. The dosage formulation of claim 1, wherein the effective dose reduces one or more risk factors or marker of coronary heart disease selected from the group consisting of leptin lowering and regulating blood pressure.

9. The dosage formulation of claim 1, wherein the effective dose reduces one or more risk factors or marker of coronary heart disease selected from the group consisting of reducing endothelial inflammation, reducing IL-6, or reducing TNF-α in CHD patients and patients showing high values of inflammatory markers, and anti-atherosclerotic properties.

10. The dosage formulation of claim 1, wherein the risk factor or marker of coronary heart disease comprises adiponectin enhancement in individuals showing low values of adiponectin.

11. The dosage formulation of claim 1, wherein the effective dose reduces one or more risk factors or marker of coronary heart disease selected from the group consisting of anti-atherogenic, hypolipidemic, anti-inflammatory, anti-anxiety, adiponectin enhancing and Hcy lowering effects.

12. The dosage formulation of claim 1, wherein the risk factor or marker is selected from the group consisting of hypolipidemic effects, anti-atherogenic effects, reduction of vascular inflammation, lowering total cholesterol, lowering LDL-c, increasing cholesterol HDL-C, reducing hyper-triglyceridemia, homocysteine lowering property among the individuals showing hyper-Hcy level, anti-stress or anti-anxiety effects to improve sleep pattern, lowering blood glucose, reducing triglycerides, leptin lowering, regulating blood pressure, reducing endothelial inflammation, reducing IL-6 or reducing TNF-α in patients showing high values of inflammatory markers, anti-atherosclerotic properties, and adiponectin enhancement in individuals showing low values of adiponectin.

* * * * *